United States Patent [19]

Taylor et al.

[11] Patent Number: 5,690,633

[45] Date of Patent: Nov. 25, 1997

[54] ORTHOPEDIC FRACTURE FIXATION DEVICE

[75] Inventors: Harold S. Taylor; J. Charles Taylor, both of Memphis, Tenn.

[73] Assignee: Smith & Nephew Richards, Inc., Memphis, Tenn.

[21] Appl. No.: 626,913

[22] Filed: Apr. 3, 1996

Related U.S. Application Data

[63] Continuation of Ser. No. 311,316, Sep. 23, 1994, abandoned.
[51] Int. Cl.$^6$ ............................................. A61B 17/60
[52] U.S. Cl. .............................. 606/73; 606/54; 606/72
[58] Field of Search .................................. 606/73, 53–4, 606/59–61, 65, 66, 69–72, 104, 154, 156, 150

Primary Examiner—Michael Buiz
Assistant Examiner—Daphna Shai
Attorney, Agent, or Firm—Earl Douglas; Larry W. McKenzie

[57] ABSTRACT

An improved fracture fixation device for securing an external fixator system to bone structure and for compressing a first bone fragment of the bone structure against a second bone fragment of the bone structure. The fracture fixation device includes a screw portion for screwing into the first bone fragment; a bone engagement portion for engaging the second bone fragment and for coacting with the screw portion to compress the first bone fragment against the second bone fragment when the screw portion is screwed into the first bone fragment and the engagement portion engages the second bone fragment; and a attachment portion for attaching the engagement portion to the external fixator system.

11 Claims, 3 Drawing Sheets

ORTHOPEDIC FRACTURE FIXATION DEVICE

This application is a continuation of application Ser. No. 08/311,316, filed Sep. 23, 1994, now abandoned.

BACKGROUND OF THE INVENTION

1. Field of the Invention

The present invention relates, in general, to skeletal fixation systems and methods and, more specifically, to an improved orthopedic fracture fixation device that combines the functions of external fixation pins and internal fixation lag screws in a single unit.

2. Background Art

Fractures of bone structure can be treated surgically, inter alia, by external fixation, by internal fixation, or by osteosynthesis.

External fixation of bone fractures uses an external frame that is attached to the boney skeleton with threaded and/or smooth pins and/or threaded and/or smooth and/or beaded wires. External fixation is commonly utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixator frames vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb or may extend through the boney skeleton and out one side of the limb. Pins which extend completely through the boney skeleton and out both sides of the limb are commonly referred to as "trans fixation pins." Pins which extend through the boney skeleton and out only one side of the limb are commonly referred to as "half pins." Materials for frames also vary, including metals, alloys, plastics, composites, and ceramics. External fixators vary in their ability to accommodate different spatial relations between the pin and bar.

Mears, U.S. Pat. No. 4,620,533, issued Nov. 4, 1986, discloses one example of an external fixator. Thus, Mears discloses an apparatus for the external fixation and stabilization of a bone fracture, the apparatus including a plurality of fixation pins attached to at least one rigid bar through adjustable clamps having articulating balls which allow rotational adjustment of each pin or bar. The pins are shown in FIG. 1 of Mears as extending completely through the bone.

Internal fixation of bone fractures consist of passing a screw or bolt, etc., directly through two or more bone fragments to fasten and hold the bone fragments in close contact with one another, thereby providing interfragmentary compression. Such interfragmentary fixation can be provided using conventional lag screws, well known Herbert screws or Knowles pins, etc. Pierce, U.S. Pat. No. 2,760,488, discloses an example of internal fixation device.

Lag screws for bone fixation work like lag screws for wood. Considering the geometry of the screw with overall length, thread length, root diameter, shank diameter, head diameter, and pitch; and properly preparing the two pieces of wood or bone: two pieces of wood or bone may be brought closely together, in fact . . . lagged together. Generally, a clearance hole for the shank is made in the fragment on which the screw head will make contact, the near fragment. This hole is larger in diameter than the outer diameter of the screw shank or threads, but smaller in diameter than the head of the screw. A hole is made in the other fragment, the far fragment, which is smaller in diameter than the outer diameter of the threads. As the screw is inserted by rotating the screw it will continue to advance into the other fragment by virtue of purchase of the threads in the other fragment and the pitch of the threads. After the head of the screw abuts the near fragment, continued advancement of the screw will tend to close any gap between the fragments and may create a compressive strain between the two fragments. In practice it is not always necessary to predrill the far fragment as the screw may advance satisfactorily without predrilling. This lag effect can be achieved with a partially threaded screw as long the hole in the near fragment is larger than the non threaded shank of the screw, either by virtue of sufficiently predrilling the fragment or by virtue of the larger threaded portion of the screw having prepared a hole with its passage through the near fragment.

The term osteosynthesis refers to plating, the application of screws and strips of metal with holes to bone. Härle, U.S. Pat. No. 5,147,363, discloses an example of an osteosynthesis system including various different designs of bone screws for securing plates to bones to fix the bones and bone segments in specific position and alignment relative to one another.

In some cases, it may be necessary or desirable to both lag or compress bone fragments together using internal, interfragmentary fixation means, and provide for the overall stability by attaching the bone fragments to an external fixation frame. Traditionally, fragments would be first lagged together with conventional lag screws or Herbert type screws and then external fixation pins are inserted at different sites to allow attachment to an external frame. A typical such treatment is shown diagrammatically in FIG. 1 of the drawings. Such a treatment is shown in FIG. 1 of the drawings. Thus, FIG. 1 shows bone structure B, such as a human femur, having a first bone fragment F', a second fragment F", and a third bone fragment F'". A typical prior art lag screw L is used to provide interfragmentary fixation of the first and second bone fragments F', F" with a typical prior art external fixator system S used to provide external skeletal fixation of the first and third bone fragments F', F'". The external fixator system S shown in FIG. 1 includes an elongated external fixator bar or rod R, and a pair of external fixator connectors C attached to the external fixator rod R at spaced locations thereon. External fixator pins P extend between the external fixator connectors C and the bone structure B whereby desired force can be applied between the first and third bone fragments F', F'". It should be understood that the number of external fixator pins P used on each bone fragment can vary.

Prior art internal fixation screws (e.g., lag screws and Herbert screws) do not provide means for attachment to an external fixator frame. However, bone fragments may not be large enough to utilize both a lag screw for internal fixation thereof, and a half pin for external fixation thereof to provide overall stabilization.

Knowles pins, used only for internal lag screw fixation, include one or more circumferential grooves for purposely weakening the pins so that they can be broken off at the head, the opposite property of what is desirable for an external fixation pin. Knowles pins are not used with external fixation. Knowles pins include threaded tip, shank, head section, grooved section (for purposely weakening the shaft section) and shaft section.

Conventional lag screws can provide interfragmentary fixation, but do not allow attachment to an external skeletal fixator frame.

Herbert screws can provide interfragmentary fixation, but do not allow attachment to an external skeletal fixator frame.

With prior art utilizing half pins, two fragments could be brought into close apposition by first attaching one fragment to the external fixation frame and while attaching the second fragment to the external frame, push the fragments together before clamping onto the half pins in the second fragment. However, no interfragmentary compression and certainly no true lag effect could be accomplished unless at least one fragment was already attached to the external frame via half pins. The lag screw half pin provides a means of lagging together fragments and maintaining this lagged relation until it is possible and desirable to attach these lagged fragments to the external fixator frame. In the treatment of certain conditions or injuries, especially involving the joint surfaces, it may be necessary to accurately reduce or reappose important fragments at an earlier stage of the surgical procedure and subsequently achieve overall stability by attachment of fragments to the external frame. By utilizing the lag screw half pin, the important lagged position of key fragments can be achieved and maintained until later attachment to the external fixator frame. The external fixator frame can be an incumbrance when trying to visualize or manipulate key fragments. The lag screw half pin can be utilized to achieve and maintain this lagged position of key fragments without the incumbrance of the external frame at earlier stages.

The lag screw half pin also can be used alone without the external frame. It may be desirable to attach and lag one fragment to another and later remove the lag screw. This subsequent removal would require a subsequent incision and possibly an anesthetic. Using a lag screw half pin, the fragments may be lagged together and the pin can be removed when appropriate by unscrewing the external exposed portion of the pin.

A preliminary patentability search conducted in class 606, subclasses 65 and 73, produced the following patents which appear to be relevant to the present invention:

Purficato, U.S. Pat. No. 2,631,584, issued Jul. 22, 1948, discloses an assembly for securing fragments of a bone fracture together. The assembly includes a tubular nail for being driven through an aperture in a reinforcing plate and into a first bone fragment, and a pin mounted within the tubular nail for being pushed laterally from the distal portion of the nail after the nail has being fully driven into the bone fragment to secure the nail, and thus the reinforcing plate, to the bone fragment. In use, a second tubular nail and pin combination is used to secure the reinforcing plate to another bone fragment, thereby securing the two bone fragments together.

Pierce, U.S. Pat. No. 2,760,488, issued Aug. 28, 1956, discloses an internal bone fixation apparatus including an elongated pin having an enlarged head portion intermediate the opposite ends thereof for being inserted completely through bone structure at a fracture until the enlarged head abuts one side of the bone structure, and a nut assembly for being screwed onto the end of the pin opposite the enlarged head after the pin has been inserted completely through the bone structure to thereby compress the fracture. After the pin and nut assembly have been so secured, the opposite ends of the pin and any portion of the nut that extends to or beyond the patient's skin are cut off below the patient's skin with nippers.

Charnley, U.S. Pat. No. 2,801,631, issued Aug. 6, 1957, discloses a threaded rod and nut assembly used in combination with a plate specifically designed to hold fractured portions of the head of a femur together.

Wagenknecht, U.S. Pat. No. 4,978,350, issued Dec. 18, 1990, discloses a self tapping, transcutaneous external fixation pin for use with an external skeletal fixation appliance.

Perren, U.S. Pat. No. 5,019,078, issued May 28, 1991, discloses a bone screw of the so-called Schanz type, having a smooth shank segment, a threaded segment, and a tapered transition segment between the shaft and the threaded segment.

Stednitz, U.S. Pat. No. 5,098,435, issued Mar. 24, 1992, discloses a bone stabilizing system including hollow or cannulated lag screw.

Härle, U.S. Pat. No. 5,147,363, issued Sep. 15, 1992, discloses an osteosynthetic screw for the setting of bones or bone fragments. In the embodiments shown in FIGS. 3, 6, and 7 of the Härle patent, the osteosynthetic screw has a threaded proximal end for screwing into a bone, and a threaded distal end or extension for allowing a osteosynthetic plate and cover plate assembly to be secured thereto.

Nothing in the known prior art discloses or suggests the present invention. More specifically, nothing in the known prior art discloses or suggests a fracture fixation device for securing an external fixator system to bone structure and for compressing a first bone fragment of the bone structure against a second bone fragment of the bone structure; and including screw means for screwing into the first bone fragment; engagement means for engaging the second bone fragment and for coacting with the screw means to compress the first bone fragment against the second bone fragment when the screw means is screwed into the first bone fragment and the engagement means engages the second bone fragment; and attachment means for attaching the engagement means to the external fixator system.

SUMMARY OF THE INVENTION

The present invention provides a novel form of skeletal fixation that combines the effects of internal or lag screw fixation and external skeletal fixation or support.

The fracture fixation device of the present invention includes, in general, screw means for screwing into a first bone fragment; engagement means for engaging a second bone fragment and for coacting with the screw means to compress the first bone fragment against the second bone fragment when the screw means is screwed into the first bone fragment and the engagement means engages the second bone fragment; and attachment means for attaching the engagement means to an external fixator system.

One object of the present invention is to provide a novel lag screw half pin for use with external fixation. By virtue of its larger central dimension the pin can act as a true lag screw with either partial or full threads beyond the enlarged central portion or head. The lag effect would depend upon proper purchase in the distal fragment and sufficient clearance in the proximal fragment and sufficient compressive contact of the enlarged central portion or head against the near fragment. This lag effect or ability to bring fragments close together is accomplished independent of additional lag effect the external fixation system may or might not provide. The head portion may be of varied shape to ease later extraction through soft tissues. This pin will have additional shank material to one side of the central enlargement on the side opposite the threaded portion. This extension may be attached to an external fixation frame which provides support for the skeleton.

Another object of the present invention is to provide a novel lag screw transfixation pin for use with external fixation. This pin is similar to the lag screw half pin but will further have additional shank or shaft material on the end of the threaded portion opposite the central enlargement for extending through the limb and for additional attachment to a second unilateral frame or to a circumferential external frame.

Another object of the present invention is to provide an orthopedic external fixator pin that permits an interfragmentary lag effect to be created between indicated fragments and provides for attachment to an external fixation device.

Another object of the present invention is to provide an orthopedic external fixator pin that eases spatial and sequential constraints of existing art and potentially decrease the materials cost of treating an appropriate situation.

Another object of the present invention is to provide the necessary functions of both a lag screw and a half pin in the space of only one so that bone fragments can be drawn together and compressive strain applied thereto using the same attachment means for attaching an external fixator frame to the bone structure.

DESCRIPTION OF THE PREFERRED EMBODIMENTS

Figure 1:
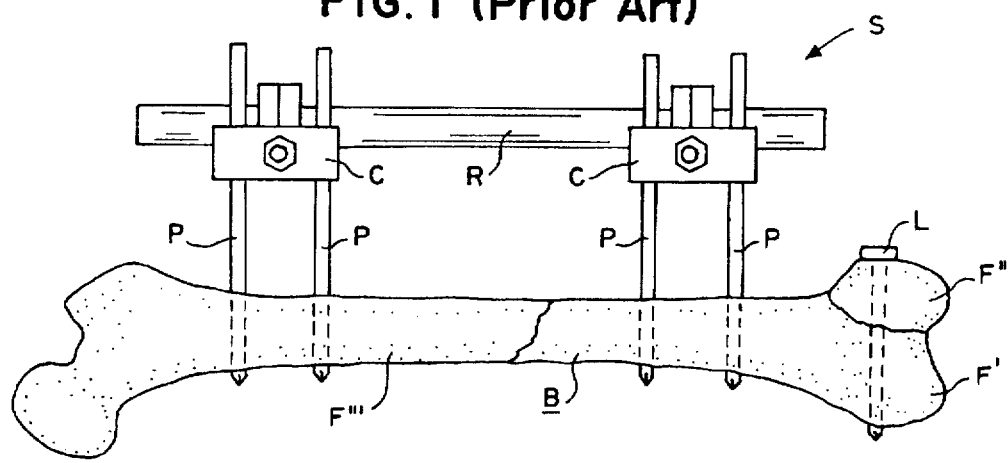
FIG. 1 is a diagrammatic elevation view of a typical prior art orthopedic external fixator system and a typical prior art orthopedic lag screw shown in combination with a comminuted fractured femur.
Figure 2:
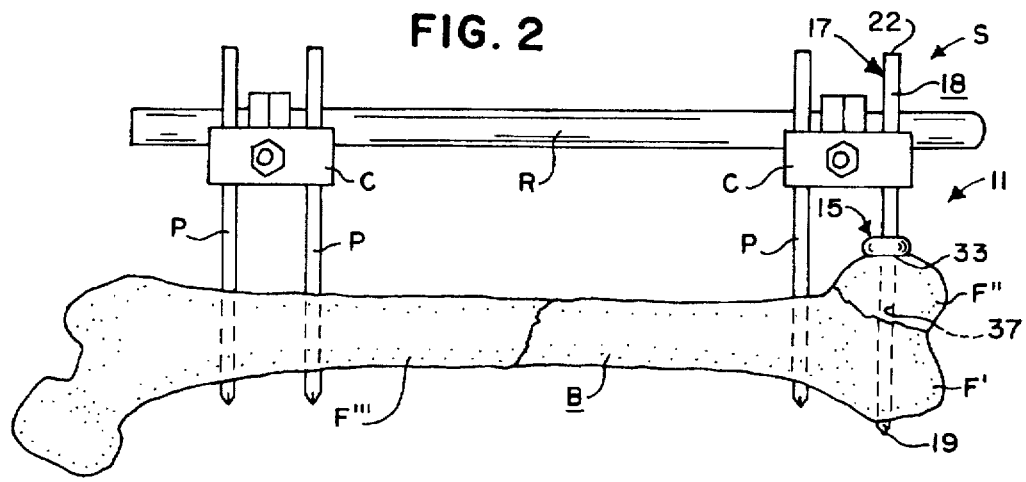
FIG. 2 is a diagrammatic elevation view similar to FIG. 1 but showing a first embodiment of the improved orthopedic fracture fixation device of the present invention in combination with the frame of orthopedic external fixator system and the comminuted fractured femur.

The improved orthopedic fracture fixation device 11 of the present invention is shown in FIG. 2 in combination with an external fixator system S and bone structure B, such as a human femur. The external fixator system S shown in FIG. 2 includes an elongated external fixator bar or rod R, and at least a pair of external fixator connectors C attached to the rod R at spaced locations thereon. A first fixation device such as a typical external fixator pin P is shown in FIG. 2 having a tip end secured to the third bone fragment F''' of the bone structure B, and having an outer end secured to one of the connectors C of the external fixator system S. The fracture fixation device 11 of the present invention is shown in FIG. 2 as forming a second fixation device having a tip end secured to the first bone fragment F', an outer end secured to one of the connectors C of the external fixator system S, and a midportion engaging the second bone fragment F''. It should be noted that the number of external fixator pins P and/or fracture fixation devices 11 used with each bone fragment may vary as will now be apparent to those skilled in the art.

The fracture fixation device 11 of the present invention includes screw means 13 for screwing into the first bone fragment F'; engagement means 15 for engaging the second bone fragment F'' and for coacting with the screw means 13 to compress the first and second bone fragments F', F'' against one another when the screw means 13 is screwed into the first bone fragment F' and the engagement means 15 engages the second bone fragment F''; and attachment means 17 for attaching the engagement means 15 to the external fixator system S.

The screw means 13 and attachment means 17 are preferably constructed as an integral, one-piece elongated unit or rod 18 including a tip end 19, an external threaded portion 21 for screwing into the bone structure B, and an outer end 22 for being secured to an external fixator system S. That is, the outer end 22 of the rod 18 may be clamped or otherwise secured to an external fixator connector C of an external fixator system S as shown in FIG. 2. The threaded portion 21 of the rod 18 forms the screw means 13 and may be self-tapping so that the screw means 13 can be screwed into the bone structure B without requiring a pilot hole to be first formed into the bone structure B. The rod 18 may include a shank portion 23 between the threaded portion 21 and the engagement means 15. The shank portion 23 may be smaller in outer diameter than the screw means 13 as shown, for example, in FIGS. 3, 4, 8, 10 and 17.

The fracture fixation device 11 may have a longitudinal passageway 24 extending completely therethrough (see FIGS. 3 and 4) for allowing the screw means 13 to be screwed into the first bone fragment F' over a guide pin as will now be apparent to those skilled in the art.

Figure 11:
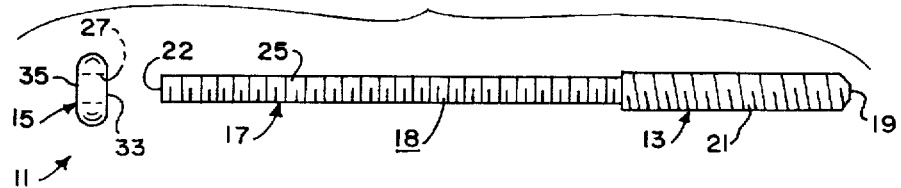
FIG. 11 is an exploded front elevation view of a seventh embodiment of the improved orthopedic fracture fixation device of the present invention.
Figure 12:
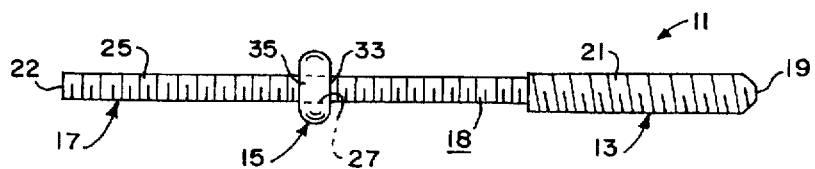
FIG. 12 is a front elevation view of the seventh embodiment of the improved orthopedic fracture fixation device of the present invention.
Figure 13:
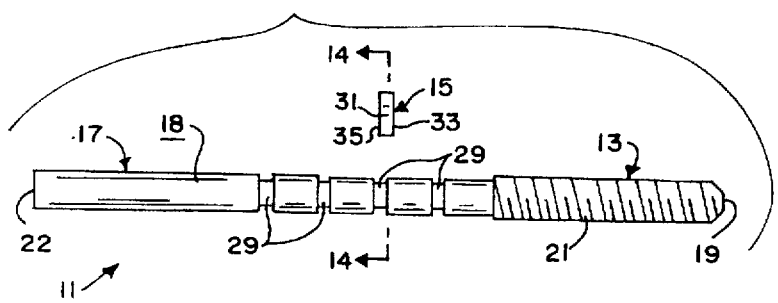
FIG. 13 is an exploded front elevation view of an eighth embodiment of the improved orthopedic fracture fixation device of the present invention.
Figure 14:
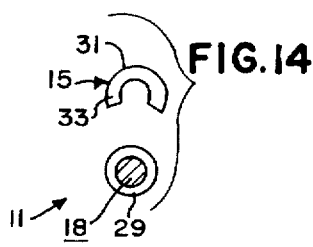
FIG. 14 is a sectional view substantially as taken on line 14—14 of FIG. 13.
Figure 15:
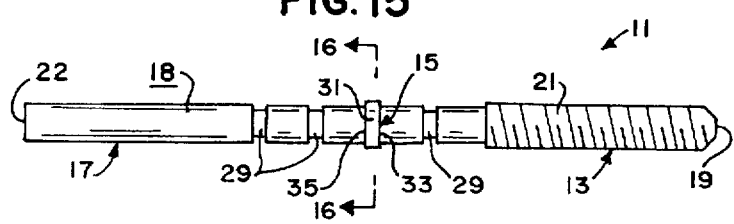
FIG. 15 is a front elevation view of the eighth embodiment of the improved orthopedic fracture fixation device of the present invention.
Figure 16:
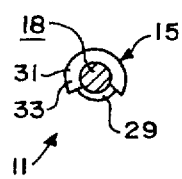
FIG. 16 is a sectional view substantially as taken on line 16—16 of FIG. 15.

The engagement means 15 may be constructed as a one-piece, integral unit with the screw means 13 and the attachment means 17; may be manufactured separate from the rod means 18 and press-fitted there onto; or may be adjustably attached to the rod 18 so that the effective length of the screw means 13 can be varied. For example, the outer end 22 of the rod 18 may have external threads 25 thereon as shown in FIGS. 11 and 12 and the engagement means 15 may consist of a nut-like member having a threaded aperture 27 therethrough for be screwably received on the external threads 25 in a manner that allows the position of the engagement means 15 on the rod 18 to be easily varied by merely rotating the engagement means 15 on the rod 18 as will now be apparent to those skilled in the art. Also, rather than being screwably attached to the rod 18, the engagement means 15 may be frictionally attached to the rod 18 in a manner that allows the position of the engagement means 15 on the rod 18 to be easily varied. Thus, for example, as shown in FIGS. 13–16, the rod 18 may have a plurality of spaced grooves 29 therein, preferably transverse to the longitudinal axis thereof; and the engagement means 15 preferably includes a C-shaped body 31 for adjustably fitting into one of the plurality of spaced grooves 29 so that the position of the engagement means 15 on the rod 18 can be easily varied by merely moving the C-shaped body 31 from one groove 29 to another as will now be apparent to those skilled in the an.

Figure 6:
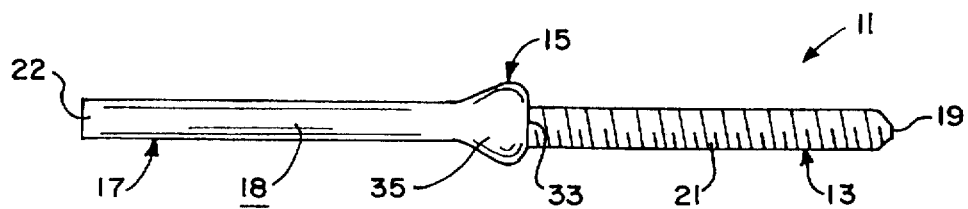
FIG. 6 is a front elevation view of a second embodiment of the orthopedic external fixation pin of the present invention.

The engagement means 15 may be formed as an enlarged collar or the like on the rod 18 between the screw means 13 and the attachment means 17, and may have a face surface 33 with a planar portion for abutting the second bone fragment F", and a back surface 35. The back surface 35 may have a planar portion as shown in FIGS. 2, 3, 4, 11, 12, 13, and 15, or may have a conical portion as shown in FIG. 6.

Figure 8:
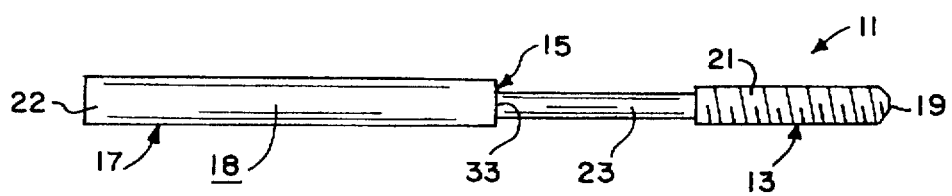
FIG. 8 is a front elevation view of a fourth embodiment of the improved orthopedic fracture fixation device of the present invention.
Figure 9:
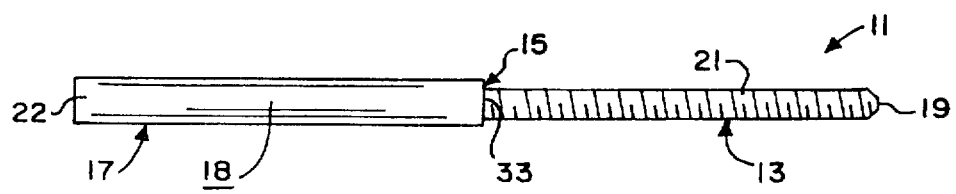
FIG. 9 is a front elevation view of a fifth embodiment of the improved orthopedic fracture fixation device of the present invention.
Figure 10:
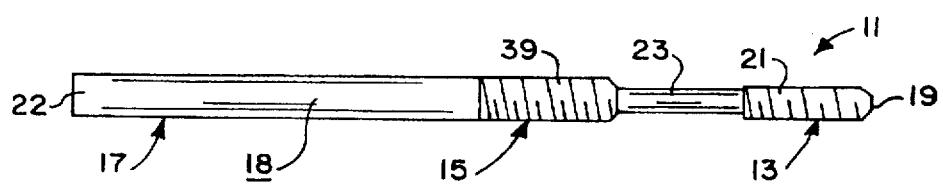
FIG. 10 is a front elevation view of a sixth embodiment of the improved orthopedic fracture fixation device of the present invention.

On the other hand, the outer diameter of the engagement means 15 may be the same as the outer diameter of the attachment means 17 as shown in FIGS. 8, 9, and 10.

The fracture fixation device 11 can be made in any manner and out of any medical grade biocompatible metal or the like as any other medical screw. Using a lathe, the fracture fixation device 11 can be turned from a single piece of biocompatible material with threads. Alternatively, threads can be cut into a previously formed body by a tap or thread mill. The screw means 13, engagement means 15, and attachment means 17 can be machined as an integral, one piece unit or construction. Conversely, the screw means 13 and attachment means 17 can be machined as an integral, one piece unit or construction (i.e., as the one piece rod 18); and the engagement means 15 can be machined as a separate part and permanently attached to the rod 18 by soldering, welding or press fit, continuously adjustably attached to the rod 18 by coacting threads, or incrementally adjustably attached to the rod 18 as a snap ring for being clipped into position in grooves in the rod 18, etc.

The specific size of the fracture fixation device 11 can vary depending on the size of the bone fragments, etc.

Figure 3:
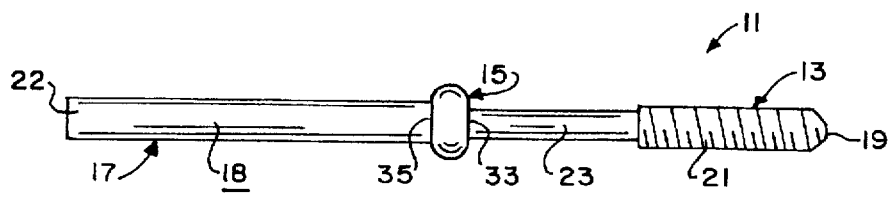
FIG. 3 is a front elevation view of the first embodiment of the improved orthopedic fracture fixation device of the present invention.

The embodiment of the fracture fixation device 11 shown in FIGS. 2 and 3 may have an attachment means 17 that is 6 millimeters in diameter, a head or engagement means 15 that is 12 millimeters in diameter, a shank portion 23 that is 5 millimeters in diameter, and a threaded portion 21 that is 6.4 millimeters in diameter. To secure the bone fragments F', F" together using this embodiment of the fracture fixation device 11, a pilot hole 37, approximately equal in diameter to the minor thread diameter of the threaded portion 21 is made in both fragments F', F". A thread tap may be used to prepare threads in the pilot hole 37 or the threaded portion 21 may be self tapping as hereinabove stated. The rod 18 is rotated by, for example, a manual or motorized tool attached to the outer end 22 thereof with an appropriate chuck or the like as will now be apparent to those skilled in the art. In any event, as the rod 18 is rotated, it will advance into the bone fragments F', F" by means of the threaded portion 21. After the engagement means 15 abuts the outer surface of the bone structure B (e.g., the near cortex of the bone fragment F"), continued rotation will tend to compress or lag the fragments F', F" together. The attachment means 17 can then be connected to an external fixator system S in a typical manner (e.g., by inserting the outer end 22 of the rod 18 into an external fixator connector C of the system S).

The embodiment of the fracture fixation device 11 shown in FIG. 6 may have an attachment means 17 that is 6 millimeters in diameter, an engagement means 15 that is 12 millimeters in diameter in the shape of a well known Gemini capsule head, and a threaded portion 21 that is 6.4 millimeters in diameter extending completely between the face surface 33 of the engagement means 15 to the tip end 19 of the rod 18. To secure the bone fragments F', F" together using this embodiment of the fracture fixation device 11, a pilot hole is drilled in both bone fragments F', F". The pilot hole in the bone fragment F" is preferably enlarged to form a clearance hole with a diameter greater than the outer diameter of the threaded portion 21 but smaller than the diameter of the engagement means 15. As the device 11 is inserted by rotation, the engagement means 15 will abut the near cortex of the bone fragment F" and compress or lag the fragments F', together by virtue of thread purchase in the bone fragment F', clearance hole in the bone fragment F" and the abutment of the engagement means 15 against the cortex or outer surface of the bone fragment F".

Figure 7:
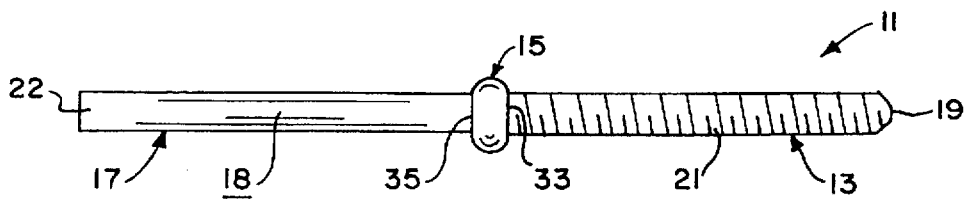
FIG. 7 is a front elevation view of a third embodiment of the improved orthopedic fracture fixation device of the present invention.

The embodiment of the fracture fixation device 11 shown in FIG. 7 may have an attachment means 17 that is 6 millimeters in diameter, an engagement means 15 that is 12 millimeters in diameter, and a threaded portion 21 extending completely between the face surface 33 of the engagement means 15 and the tip end 19 of the rod 18 that is 6 millimeters in diameter. This embodiment of the fracture fixation device 11 can be used in the same manner as hereinabove described relative the embodiment shown in FIG. 6 to secure the bone fragments F', F" together.

The embodiment of the fracture fixation device 11 shown in FIG. 8 may have an attachment means 17 that is 7 millimeters in diameter, a shank portion 23 that is 4 millimeters in diameter, and a threaded portion 21 that is 5 millimeters in diameter. An effective engagement means 15 is provided by the step off at the junction of the attachment means 17 and the shank portion 23 with the step off forming the face surface 33 of the engagement means 15. This embodiment of the fracture fixation device 11 can be used in the same manner as hereinabove described relative the embodiment shown in FIGS. 2 and 3 to secure the bone fragments F', F" together.

The embodiment of the fracture fixation device 11 shown in FIG. 9 may have an attachment means 17 that is 7 millimeters in diameter, and a threaded portion 21 that is 5 millimeters in diameter and that extends completely from the face surface 33 of the engagement means 15 to the tip end 19 of the rod 18. As in the embodiment shown in FIG. 8, an effective engagement means 15 is provided by the step off at the junction of the attachment means 17 and the shank portion 23 with the step off forming the face surface 33 of the engagement means 15. This embodiment of the fracture fixation device 11 can be used in the same manner as hereinabove described relative the embodiment shown in FIGS. 6 and 7 to secure the bone fragments F', F'" together.

The embodiment of the fracture fixation device 11 shown in FIG. 10 may have an attachment means 17 that is 6 millimeters in diameter, a shank portion 23 that is 4 millimeters in diameter, and a threaded portion 21 that is 5 millimeters in diameter. In addition, the engagement means 15 of this embodiment is 6 millimeters in diameter and has external threads 39 thereon with a differential between the thread pitch of the threaded portion 21 and the external threads of the engagement means 15. More specifically, the pitch of the threaded portion 21 is greater that the pitch of the external threads 39 of the engagement means 15. Thus, an effective engagement means 15 is provided by the differential thread pitch between the threaded portion 21 and the external threads 39 of the engagement means 15. Depending upon the density of the bone fragments F', F'", predrilling may be required with a drill approximately equal in diameter to the root diameter of the threaded portion 21. In bone structure B with less density, this embodiment may be inserted by virtue of a self tapping tip. As the external threads 39 of the engagement means 15 enters the second bone fragment F'", the fragments F', F'" will be compressed or lagged together by virtue of thread purchase of the threaded portion 21 in the bone fragment F' and the greater thread purchase of the external threads 39 of the engagement means 15 in the bone fragment F'".

The embodiment of the fracture fixation device 11 shown in FIGS. 11 and 12 may have an attachment means 17 that is 5 millimeters in diameter, a threaded portion 21 that is 6.4 millimeters in diameter with the attachment means 17 having external machine threads thereon extending completely between the threaded portion 21 and the outer end 22 of the rod 18, and an engagement means 15 that is 12 millimeters in diameter with a threaded aperture for being coacting with the external threads of the attachment means 17. With the engagement means 15 screwed onto the attachment means 17, this embodiment of the fracture fixation device 11 can be used in the same manner as hereinabove described relative the embodiment shown in FIGS. 2 and 3 to secure the bone fragments F', F' together. However, the threaded attachment of the engagement means 15 onto the attachment means 17 allows continuous adjustment of the face surface 33 of the engagement means 15 relative to the tip end 19 of the rod 18. Additionally, after so compressing or lagging the fragments F', F' together, and even after attaching the fracture fixation device 11 to the external fixator system S, the engagement means 15 can be further adjusted to increase or decrease the compression or lag effect by merely rotating the engagement means 15 relative to the rod 18.

The embodiment of the fracture fixation device 11 shown in FIGS. 13–16 may have an attachment means 17 that is 6 millimeters in diameter, a threaded portion 21 that is 6.4 millimeters in diameter with the attachment means 17 having a plurality of spaced slots or grooves 29 machined therein, and an engagement means 15 consisting of a C-shaped snap ring or body 31 having a nominal 10 millimeter diameter for being snapped into a selected one of the grooves 29. With the C-shaped body 31 snapped into one of the grooves 29, this embodiment of the fracture fixation device 11 can be used in the same manner as hereinabove described relative the embodiment shown in FIGS. 2 and 3 to secure the bone fragments F', F' together. However, the snap-on attachment of the engagement means 15 to the attachment means 17 allows incremental adjustment of the face surface 33 of the engagement means 15 relative to the tip end 19 of the rod 18.

Figure 4:
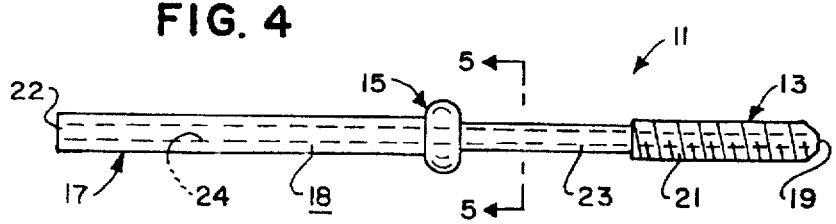
FIG. 4 is a front elevation view of a modified version of the first embodiment of the improved orthopedic fracture fixation device of the present invention.
Figure 5:
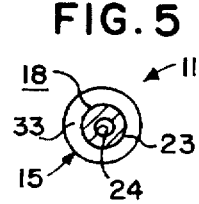
FIG. 5 is a sectional view substantially as taken on line 5—5 of FIG. 4.

The embodiment of the fracture fixation device 11 shown in FIGS. 4 and 5 may be identical to the embodiment of the fracture fixation device 11 shown in FIGS. 2 and 3 except that the fracture fixation device 11 shown in FIGS. 4 and 5 has a longitudinal passageway 24 or cannulation drilled or otherwise formed completely therethrough for allowing the screw means 13 to be screwed into the first bone fragment F' over a guide pin as will now be apparent to those skilled in the art. That is, to secure the bone fragments F', F' together using this embodiment of the fracture fixation device 11, a guide pin (not shown) is inserted into the bone fragments F', F' at the precise location it is desired to insert the screw means 13, etc. X-rays can be taken of the guide pin to insure correct and proper positioning thereof. Pilot holes or the like can then be drilled over the guide pin using cannulated drills, etc. Finally, the fracture fixation device 11 can merely be screwed into the bone structure B over the guide pin as will now be apparent to those skilled in the art. It should be understood that such longitudinal passageways or cannulation can also be formed in each embodiment of the fracture fixation device 11 shown in FIGS. 6–17 to allow such embodiments to be used with guide pins.

Figure 17:
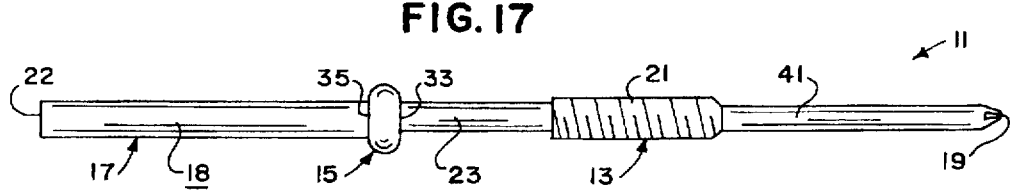
FIG. 17 is a front elevation view of a ninth embodiment of the improved orthopedic fracture fixation device of the present invention.

The embodiment of the fracture fixation device 11 shown in FIG. 17 may be identical to the embodiment of the fracture fixation device 11 shown in FIGS. 2 and 3 except that the fracture fixation device 11 shown in FIG. 17 has an additional shank or shaft portion 41 extending from the screw means 13 on the side opposite the engagement means 15 (i.e., between the threaded portion 21 and the tip end 19 of the rod 18) to transfix a patient's limb and allow the fracture fixation device 11 shown in FIG. 17 to be used as a transfixation-type external fixation pin and an internal fixation lag screw as will now be apparent to those skilled in the art. Such a fracture fixation device 11 can be used with either opposing unilateral frames on opposite sides of the limb, or a circumferential frame. That is, the tip end 19 of the rod 18 that extends through the limb can be attached to either an opposing unilateral frame by way of an external fixator connector C or the like, or both ends 19, 22 of the rod 18 could be attached to a circumferential frame as will now be apparent to those skilled in the art. The shaft portion 41 is smaller in outer diameter than the screw means 13 as clearly shown in FIG. 17. Thus, the preferred diameter of the shaft portion 41 is approximately equal to the root diameter of the adjacent threaded portion 21. More specifically, the embodiment of the fracture fixation device 11 shown in FIG. 17 may have an attachment means 17 that is 6 millimeters in diameter, a head or engagement means 15 that is 12 millimeters in diameter, a shank portion 23 that is 5 millimeters in diameter, a threaded portion 21 that is 6.4 millimeters in diameter, and a shaft portion 41 that is 5 millimeters in diameter. It should be understood that such an extended shaft portion can also be provided in each embodiment of the fracture fixation device 11 shown in FIGS. 4–16 to allow such embodiments to be used as transfixation-type external fixation pins and internal fixation lag screws.

As thus constructed and used, the present invention provides an improved fracture fixation device that provides the functions of both external fixation pins and internal fixation lag screws in a single unit. When performing external skeletal fixation, usually two pins are used to secure the external frame to each major fragment. One or more major fragments may need to be built up from smaller important fragments, especially those involving the joint surfaces. The improved fracture fixation device of the present invention can be used to draw such fragments together and to provide one attachment to the external frame. The second attachment for the external frame can also consist of a fracture fixation device of the present invention or may consist of a traditional external fixator pin. These two attachments to the external frame provide overall support for the bone structure. In addition, the fracture fixation device of the present invention can be utilized as a traditional external fixator pin simply by inserting it only partially into the bone structure such that the engagement means thereof does not impinge or engage the bone structure.

Although the present invention has been described and illustrated with respect to preferred embodiments and preferred uses therefor, it is not to be so limited since modifications and changes can be made therein which are within the full intended scope of the invention.

I claim:

1. An improved fracture fixation device for securing an external fixator system to a multiple fractured bone structure having a first bone fragment, a second bone fragment and a third bone fragment and for compressing said first bone fragment against said second bone fragment said fracture fixation device comprising:

(a) a screw portion for screwing through said second bone fragment and into the first bone fragment;

(b) a shank portion attached to said screw portion said shank portion having a smaller cross sectional area than said screw portion (c) engagement means attached to said shank portion for engaging the second bone fragment and for coacting with said screw portion to compress the first bone fragment against the second bone fragment when said screw portion is screwed into the first bone fragment and said engagement means engage the second bone fragment, said engagement means having a face surface with a portion for abutting the second bone fragment, said engagement means having a cross sectional area larger than the cross sectional area of said screw portion and (d) attachment means for attaching said fracture fixation device to the external fixator system, whereby said external fixator system secures said first and second bone fragments to said third bone fragment.

2. The device of claim 1 in which said fracture fixation device has a longitudinal passageway extending completely therethrough for allowing said screw portion to be screwed into the first bone fragment over a guide pin.

3. The device of claim 1 in which said screw portion and said attachment are constructed as a one-piece, integral unit.

4. The device of claim 3 in which said engagement means is adjustably attached to said one-piece, integral unit.

5. The device of claim 4 in which said engagement means is screwably attached to said one-piece, integral unit.

6. The device of claim 4 in which said engagement means is frictionally attached to said one-piece, integral unit.

7. The device of claim 1 in which said screw portion said engagement means and said attachment element are constructed as a one-piece, integral unit.

8. The device of claim 1 in which said screw portion includes a threaded portion having a proximal end and a distal end; and in which is included a shaft portion extending from said proximal end of said threaded portion.

9. The device of claim 8 in which said shaft portion is smaller in outer diameter than said screw portion.

10. A fracture fixation device for holding first and second bone fragments of a bone structure compressed against one another and for holding at least one of said first and second bone fragments in close contact with a third bone fragment of said bone structure, the combination comprising:

(a) an external fixation device including an elongated bar having a first end and a second end, a first connector attached to said first end of said bar, and a second connector attached to said second end of said bar;

(b) a first fixation device having a first end for securing to said third bone fragment of said bone structure and having a second end secured to said first connector of said external fixation device; and (c) a second fixation device including a screw portion for securement to said first bone fragment of said bone structure; a shank portion attached to said screw portion for extending through said second bone fragment of said bone structure without forming a purchase therebetween; and engagement means for engaging said second bone fragment and for coacting with said screw portion and said shank portion to compress said first bone fragment against said second bone fragment, said engagement means having a face surface with a portion for abutting said second bone fragment; and an attachment mechanism attaching said engagement means to said second connector of said external fixator device.

11. The device of claim 10 in which said shank portion of said second fixation device has a smaller cross sectional area than said screw portion.

* * * * *